US006858833B2

(12) United States Patent
Curtis et al.

(10) Patent No.: US 6,858,833 B2
(45) Date of Patent: Feb. 22, 2005

(54) USE OF MULTIPLE OPTICAL VORTICES FOR PUMPING, MIXING AND SORTING

(75) Inventors: Jennifer E. Curtis, Chicago, IL (US); Brian A. Koss, Chicago, IL (US); David G. Grier, New York City, NY (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 10/847,042

(22) Filed: May 17, 2004

(65) Prior Publication Data

US 2004/0211889 A1 Oct. 28, 2004

Related U.S. Application Data

(63) Continuation of application No. 10/050,213, filed on Jan. 16, 2002, now Pat. No. 6,737,634.

(51) Int. Cl.[7] .................................................. H01J 40/14
(52) U.S. Cl. ........................................ 250/221; 250/216
(58) Field of Search ................................ 250/221, 216, 250/573, 574; 359/563, 566; 356/440, 441; 209/3.1, 3.2, 5

(56) References Cited

U.S. PATENT DOCUMENTS 6,626,546 B2 * 9/2003 Grier et al. ................ 359/614

* cited by examiner

*Primary Examiner*—Que T. Le
(74) *Attorney, Agent, or Firm*—Foley & Lardner

(57) ABSTRACT

A method for creating large numbers of high-quality optical traps in arbitrary three-dimensional configurations and dynamically reconfiguring the traps under computer control. The method uses computer-generated diffractive optical elements to convert one or more optical tweezers into one or more optical vortices. The method involves combining the optical vortex technique with the holographic optical tweezer technique to create multiple optical vortices in arbitrary configurations. The method also involves employing the rotation induced in trapped particles by optical vortices to assemble clusters of particles into functional micromachines, to drive previously assembled micromachines, to pump fluids through microfluidics channels, to control flows of fluids through microfluidics channels, to mix fluids within microfluidics channels, to transport particles, to sort particles and to perform other related manipulations and transformations on matter over length scales.

13 Claims, 10 Drawing Sheets

USE OF MULTIPLE OPTICAL VORTICES FOR PUMPING, MIXING AND SORTING

CROSS-REFERENCE TO RELATED PATENT APPLICATIONS

This application is a Continuation of U.S. application Ser. No. 10/050,213, filed Jan. 16, 2002 now U.S. Pat. No. 6,737,634, incorporated herein by reference in its entirety.

This work was funded by the National Science Foundation through Grant Number DMR-9730189, and by the MRSEC program of the National Science Foundation through Grant Number DMR-980595. The government has certain rights in this invention.

FIELD OF THE INVENTION

The present invention is directed generally to the field of optical trapping techniques. More particularly, the present invention relates to techniques for manipulating particles and fluids using the torques and forces exerted by optical vortex traps.

BACKGROUND OF THE INVENTION

Optical tweezers use forces exerted by intensity gradients in strongly focused beams of light to trap and selectively move microscopic volumes of matter. Capable of applying precisely controlled forces to particles ranging in size from several to tens of nanometers to tens of micrometers, single optical tweezers have been adopted widely in biological and physical research. Holographic optical tweezers expand upon these capabilities by creating large numbers of optical traps in arbitrary three-dimensional configurations using a phase-modulating diffractive optical element (DOE) to craft the necessary intensity profile. Originally demonstrated with microfabricated diffractive optical elements, holographic optical tweezers have been implemented by encoding computer-designed patterns of phase modulation into the orientation of liquid crystal domains in spatial light modulators. Projecting a sequence of trapping patterns with a spatial light modulator dynamically reconfigures the traps.

Each photon absorbed by a trapped particle transfers its momentum to the particle and tends to displace it from the trap. If the trapping beam is circularly polarized, then each absorbed photon also transfers one quantum, $\hbar$, of angular momentum to the absorbed particle. The transferred angular momentum causes the trapped particle to rotate in place at a frequency set by the balance between the photon absorption rate and viscous drag in the fluid medium. Laguerre-Gaussian modes of light can carry angular momentum in addition to that due to polarization. Bringing such a Laguerre-Gaussian beam to a diffraction-limited focus creates a type of optical trap known as an optical vortex. In additional to carrying angular momentum, optical vortices have other properties useful for assembling and driving micromachines, for pumping and mixing fluids, for sorting and mixing particles, and for actuating microelectromechanical systems.

SUMMARY OF THE INVENTION

The present invention describes a practical and general implementation of dynamic holographic optical tweezers capable of producing hundreds and even thousands of independent traps for all manner of materials and applications.

Unlike conventional micromanipulators, dynamic holographic optical tweezers are highly reconfigurable, operate noninvasively in both open and sealed environments, and can be coupled with computer vision technology to create fully automated systems. A single apparatus thus can be adapted to a wide range of applications without modification. Dynamic holographic optical tweezers have widespread applications in biotechnology. The availability of many independent optical manipulators offers opportunities for deeply parallel high throughput screening, surgical modifications of single cells, and fabrication of widespectrum sensor arrays. In materials science, the ability to organize disparate materials into three-dimensional structures with length scales ranging from tens of nanometers to hundreds of micrometers constitutes an entirely new category of fabrication processes with immediate applications to photonics and fabrication of functional nanocomposite materials.

The applications described herein take advantage of a related method for transferring angular momentum to optically trapped particles. The technique uses computer-generated diffractive optical elements to convert a single beam into multiple traps, which in turn are used to form one or more optical vortices. The present invention involves combining the optical vortex technique with the holographic optical tweezer technique to create multiple optical vortices in arbitrary configurations. The present invention also involves employing the rotation induced in trapped particles by optical vortices to assemble clusters of particles into functional micromachines, to drive previously assembled micromachines, to pump fluids through microfluidics channels, to control flows of fluids through microfluidics channels, to mix fluids within microfluidics channels, to transport particles, to sort particles and to perform other related manipulations and transformations on matter over length scales ranging from roughly 5–10 nm to roughly 100 $\mu$m. Several applications and related extensions derive from the properties of optical vortices.

Other features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The foregoing advantages and features of the invention will become apparent upon reference to the following detailed description and the accompanying drawings, of which.

DETAILED DESCRIPTION OF THE INVENTION

Figure 1:
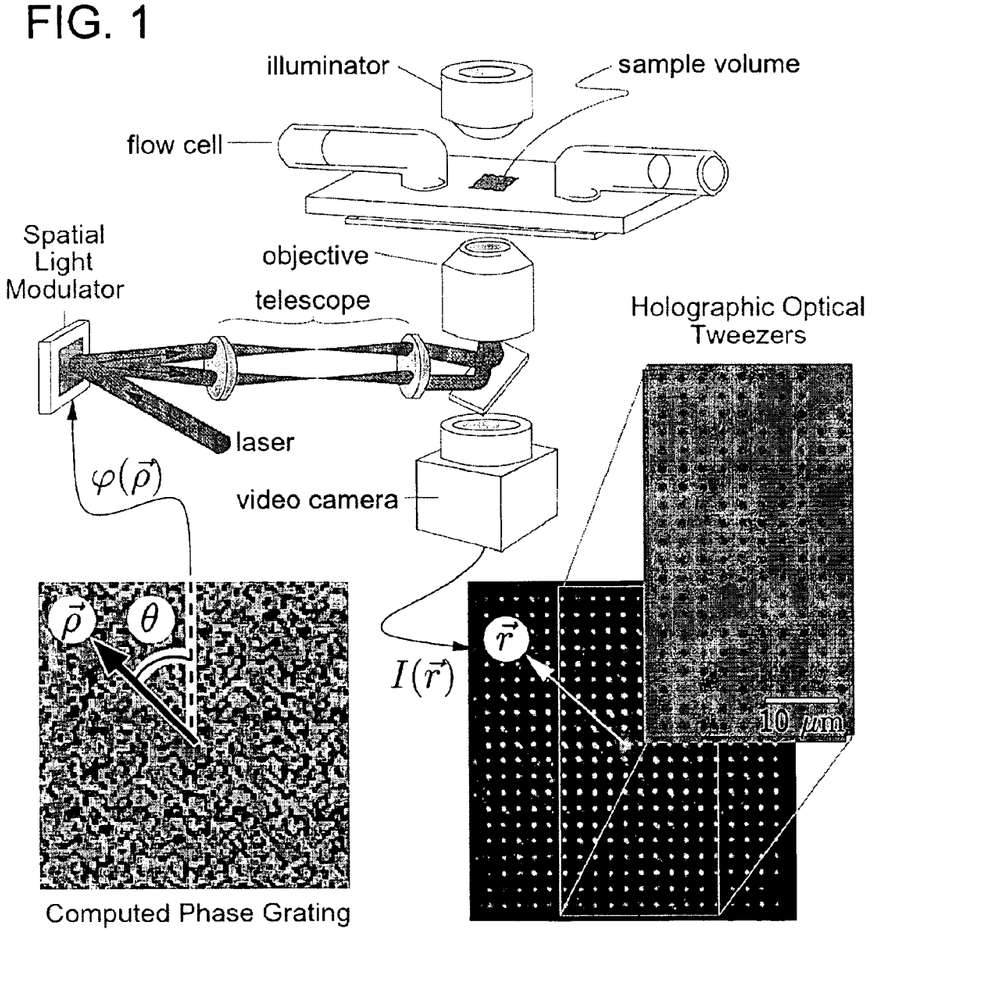
FIG. 1 is a schematic implementation of dynamic holographic optical tweezers using a reflective liquid crystal spatial light modulator to create multiple laser beams from a single input beam.

FIG. 1 is a schematic implementation of a preferred form of dynamic holographic optical tweezer system 10 using a reflective liquid crystal spatial light modulator 12 to create multiple laser beams from a single input beam. The inset phase grating of the modulator 12 is ⅕ of the hologram $\phi(\vec{\rho})$ encoding a 20×20 array of traps, with white regions corresponding to local phase shifts of $2\pi$ radians and back to 0. The beams 14 formed by the diffractive optical element are relayed by a telescope to the back aperture of a high-numerical-aperture objective lens 18 which focuses them into optical traps. The inset video micrographs show the diffraction-limited focal points reflected off a mirrored surface placed in the object plane, as well as 200 colloidal polystyrene spheres 800 nm in diameter trapped in the pattern.

Holographic optical tweezers make use of the same physical principles as concentrated optical tweezers. A dielectric particle approaching the optical tweezer system is polarized by the light's electric field. The resulting electric dipole is drawn up intensity gradients to the focus where it is trapped. This optical gradient force competes with radiation pressure which tends to displace the trapped particle along the beam's axis. Stable trapping is possible only if the focused beam's axial intensity gradient is large enough. For this reason, optical tweezers are conventionally constructed around microscope objectives with large numerical apertures and minimal aberrations.

An optical trap may be placed anywhere within the objective lens' focal volume by appropriately selecting the input beam's propagation direction and degree of collimation. For example, the collimated beam 20 entering the back aperture of the infinity-corrected objective lens 18 comes to a focus in the center of the lens' focal plane while another beam entering at an angle comes to a focus off-center. A slightly diverging beam focuses downstream of the focal plane while a converging beam focuses upstream. Multiple beams entering the lens' input pupil simultaneously each form optical traps in the focal volume, each at a location determined by its angle of incidence. The holographic optical tweezer technique uses a phase modifying diffractive optical element to impose the phase pattern for multiple beams traveling in disparate directions onto the wavefront of a single input beam, thereby transforming the single beam into multiple traps.

In the implementation depicted in FIG. 1, the diffractive optical element's function is performed by a Hamamatsu X7550 phase-only spatial light modulator 22 (SLM) capable of encoding 256 phase levels ranging from 0 to $2\pi$ radians onto light of wavelength $\lambda$=532 nm at each 40 $\mu$m phase pixel in a 480×480 array. The phase shift imposed at each pixel is specified through a computer interface with an effective refresh rate of 3 Hz for the entire array. In this particular preferred implementation, the focusing element is a Zeiss 100×NA 1.4 oil immersion objective mounted on an Axiovert S100 TV microscope 24. A dichroic mirror 26 reflects laser light into the objective lens 18 while allowing images of the trapped particles to pass through to a video camera 26. When combined with a 2.5× widefield video eyepiece, the optical train offers a 78×52 $\mu$m² field of view.

Modulating only the phase of the input beam is enough to establish any pattern of optical traps because trapping relies only on the beams' intensities and not on their relative phases. Amplitude modulations are not preferred because they would divert light away from the traps and diminish their effectiveness. Phase-only diffraction gratings used for establishing desired intensity patterns are known as kinoforms. The practical difficulty of identifying the phase modulation which best encodes a particular pattern of traps has limited previous holographic optical tweezer implementations to planar trapping patterns or very simple three-dimensional arrangements of just a few particles on fewer planes. The resulting traps, furthermore, were only appropriate for dielectric particles in low-dielectric media, and not for the more general class of materials including metals and particles made of absorbing, reflecting, or low-dielectric-constant materials.

The following discussion specifies one preferred method for calculating the kinoforms required for the applications considered in the invention. Generally, an incident laser beam's electric field in the diffractive optical element plane, $E_0(\vec{\rho})=A_0(\vec{\rho})\exp(i\psi)$, to have a constant phase $\psi$=0 and unit intensity in the diffractive optical element plane: $\int_\Omega |A_0(\vec{\rho})|^2 d^2\rho=1$. In this case, $\vec{\rho}$ denotes a position in the diffractive optical element's aperture $\Omega$. $A_0(\vec{\rho})$ is the realvalued amplitude profile of the input beam. The field's polarization vector is omitted without loss of generality with the understanding that polarization effects operate independently and in coordination with those considered here. The diffractive optical element then imposes onto the input beam's wavefront the phase profile $\phi_0(\vec{\rho})$, encoding the desired pattern of outgoing beams. These beams then are transferred by relay optics, depicted schematically in FIG. 1 as the simple telescope 16, to the objective lens 18 which forms them into traps.

The electric field $\in_j = \alpha_j \exp(i\phi_j)$ at each of the discrete traps is related to the electric field in the plane of the spatial light modulator by a generalized Fourier transform:

$$E(\vec{\rho}) = A(\vec{\rho})\exp(i\varphi(\vec{\rho})) \quad (1)$$

$$= \sum_{j=1}^{N} \int \in_j \delta(\vec{r}, \vec{\rho})\exp\left(i\frac{2\pi \vec{r}\cdot\vec{\rho}}{\lambda f}\right)d^3r \quad (2)$$

$$= \sum_{j=1}^{N} \in_j K_j^{-1}(\vec{r}_j, \vec{\rho})\exp\left(i\frac{2\pi \vec{r}\cdot\vec{\rho}}{\lambda f}\right)d^3r, \quad (3)$$

The kernel $K_j(\vec{r}, \vec{\rho})$ can be used to transform the j-th trap from a conventional tweezer into another type of trap, and $K_j^{-1}$ is its inverse. For conventional optical tweezers, $K_j=1$.

If $A(\vec{\rho})$ were identical to the input laser beam's amplitude profile, $A_0(\vec{\rho})$, then $\phi(\vec{\rho})$ would be the kinoform encoding the desired array of traps. Unfortunately, this is rarely the case. More generally, the spatially varying discrepancies between $A(\vec{\rho})$ and $A_0(\vec{\rho})$ direct light away from the desired traps and into ghosts and other undesirable artifacts. Although such composition of kinoforms is expedient, it works poorly for all but the simplest and most symmetric patterns. Nevertheless, it can serve as the basis for an iterative approximation scheme capable of computing highly efficient estimates for the ideal kinoform $\phi_0(\vec{\rho})$.

Following one particular approach, the phase $\phi(\vec{\rho})$ is calculated with Eq. (3) to be an estimate $\phi_n(\vec{\rho})$ for the desired kinoform and use this to calculate the fields at the trap positions given the actual laser profile:

$$\in_j^{(n)} = \int_\Omega A_0(\vec{\rho})\exp(i\varphi n(\vec{\rho}))K_j(\vec{r}_j, \vec{\rho})\exp\left(-i\frac{2\pi \vec{r}\cdot\vec{\rho}}{\lambda f}\right)d^2\rho. \quad (4)$$

The index n refers to the n-th iterative approximation to $\phi_0(\vec{\rho})$. The fraction $\Sigma_j|\in_j^{(n)}|^2 = \Sigma_j|\alpha_j^{(n)}|^2$ of the incident power actually delivered to the traps is a useful measure of the kinoform's efficiency.

The classic Gerchberg-Saxton algorithm replaces the amplitude $\alpha_j^{(n)}$ in this estimate with the desired amplitude $\alpha_j$, leaving the corresponding phase $\phi_j^{(n)}$ unchanged, and solves for estimate $\phi_{n+1}(\vec{\rho})$ using Eq. (3). This approach suffers from slow and nonmonotonic convergence, however. The alternate replacement scheme is:

$$\alpha_j^{(n+1)} = \left[(1-a) + a\frac{\alpha_j}{\alpha_j^{(n)}}\right]\alpha_j \quad (5)$$

Which leads to rapid monotonic convergence for $a \approx 0.5$. The resulting estimate for $\phi_0(\vec{\rho})$ then can be discretized and transmitted to the spatial light modulator to establish a trapping pattern. In cases where the spatial light modulator offers only a few discrete phase levels, discretization can be incorporated into each iteration to minimize the associated error. In all of the examples discussed below, the algorithm yields kinoforms with theoretical efficiencies exceeding 80% in two or three iterations.

Previously published techniques for computing holographic optical tweezer kinoforms utilize fast Fourier transforms to optimize the field over the entire trapping plane. These techniques achieve theoretical efficiencies exceeding 90%. However, such methods are appropriate only for two-dimensional patterns of conventional optical tweezers. The discrete transforms adopted in accordance with the preferred form of the present invention permit the encoding of more general patterns of optical tweezers as well as mixed arrays of different types of traps. Furthermore, the approach of the present invention can be implemented efficiently because discrete transforms are calculated only at the actual trap locations.

Figure 2A:
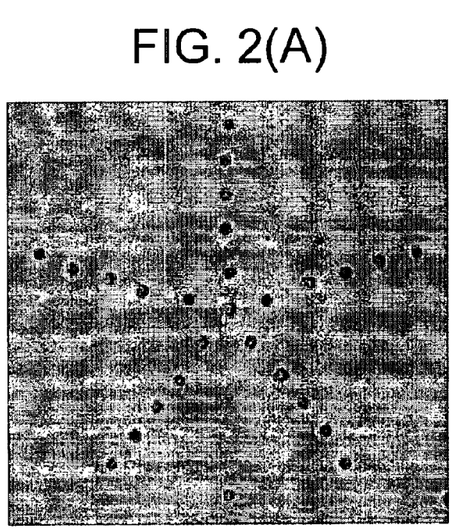
FIG. 2(A) is a pattern of 26 colloidal silica spheres 1.5 $\mu$m in diameter before transformation using dynamic holographic optical tweezers.
Figure 2B:
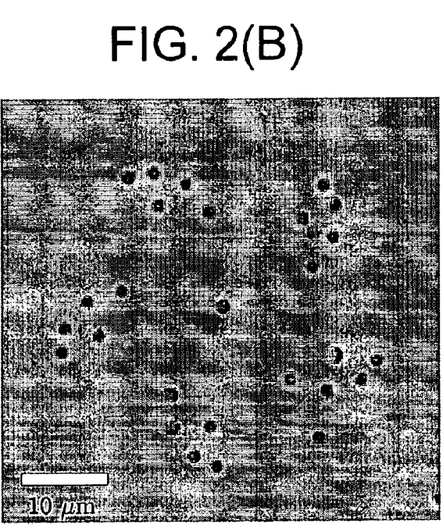
FIG. 2(B) is the same pattern after 16 steps of the transformation process.
Figure 2C:
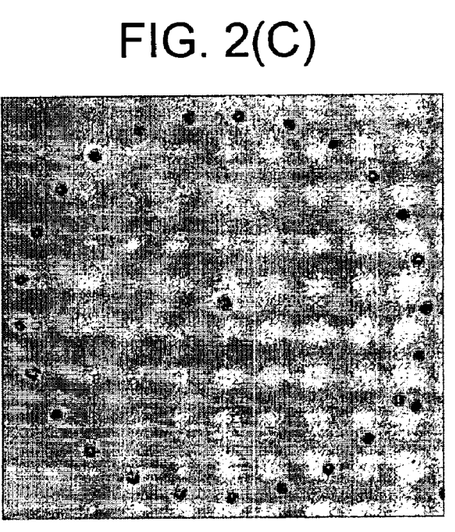
FIG. 2(C) is the final configuration of the pattern after 38 steps of the transformation process.

FIG. 2(A) shows 26 colloidal silica spheres 0.99 $\mu$m in diameter suspended in water and trapped in a planar pentagonal pattern of optical tweezers. Replacing this kinoform with another in which the taps are slightly displaced causes the spheres to hop into the next trapping pattern. Projecting a sequence of trapping patterns deterministically translates the spheres into an entirely new configuration. FIG. 2(B) shows the same spheres after 15 such hops and FIG. 2(C) after 30 such steps.

Comparable motion in the plane also can be accomplished by rapidly scanning a single tweezer through a sequence of discrete locations, thereby creating a time-shared trapping pattern. Continuous illumination of holographic optical traps offer several advantages, however. The lower peak intensities in continuous traps minimize damage to sensitive samples. Holographic optical tweezer patterns also can be more extensive than time-shared arrays which periodically release and retrieve each trapped particle.

Figure 3A:
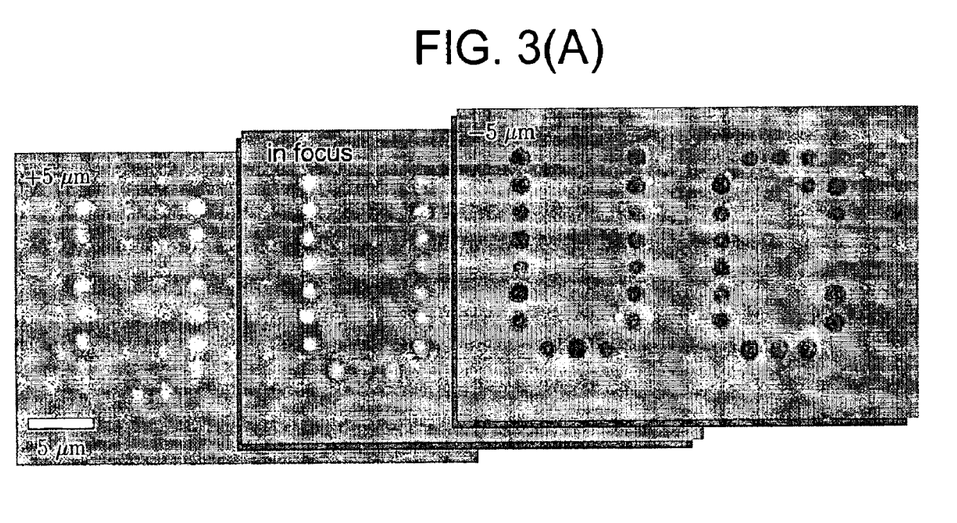
FIG. 3(A) is an image of causing incremental three-dimensional motion with holographic optical tweezers showing thirty-four 0.99 $\mu$m diameter silica spheres trapped in a single plane and then displaced by ±5 $\mu$m using Eq. (6), wherein the spheres images change in response to their displacement from the focal plane.

Furthermore, dynamic holographic optical tweezers are not limited to planar motion. If the laser beam illuminating the spatial light modulator were slightly diverging, then the entire pattern of traps would come to a focus downstream of the focal plane. Such divergence can be introduced with a Fresnel lens, encoded as a phase grating with:

$$\varphi_z(\vec{\rho}) = \frac{2\pi\rho^2}{M\lambda z}\mathrm{mod}2\pi, \quad (6)$$

where z is the desired displacement of the optical traps relative to the focal plane in an optical train with axial magnification M. In the above case, the modulo operator is understood to discretize the continuous phase profile for an optimal implementation on the phase-shifting optical element 15. Rather than placing a separate Fresnel lens into the input beam, the same functionality can be obtained by adding the lens' phase modulation to the existing kinoform: $\lfloor\phi_0(\vec{\rho})+\phi_z(\vec{\rho})\rfloor$mod $2\pi$. FIG. 3(A) shows a typical array of optical tweezers collectively displaced out of the plane in this manner. The accessible range of out-of-plane motion according to the present invention is ±10 $\mu$m.

Figure 3B:
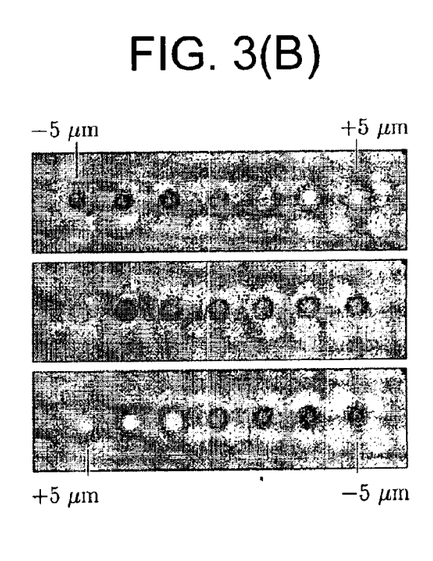
FIG. 3(B) shows seven spheres trapped simultaneously in seven different planes using kinoforms calculated with Eq. (7)

Instead of being applied to the entire trapping pattern, separate lens functions can be applied to each trap individually by including the kernels $$K_j^z(\vec{r}_j, \vec{p}) \exp\left(i \frac{2\pi \rho^2}{M \lambda z_j}\right) \quad (7)$$

in Eqs. (3) and (4). FIG. 3(B) shows seven spheres simultaneously positioned in seven different planes in this way.

Figure 5:
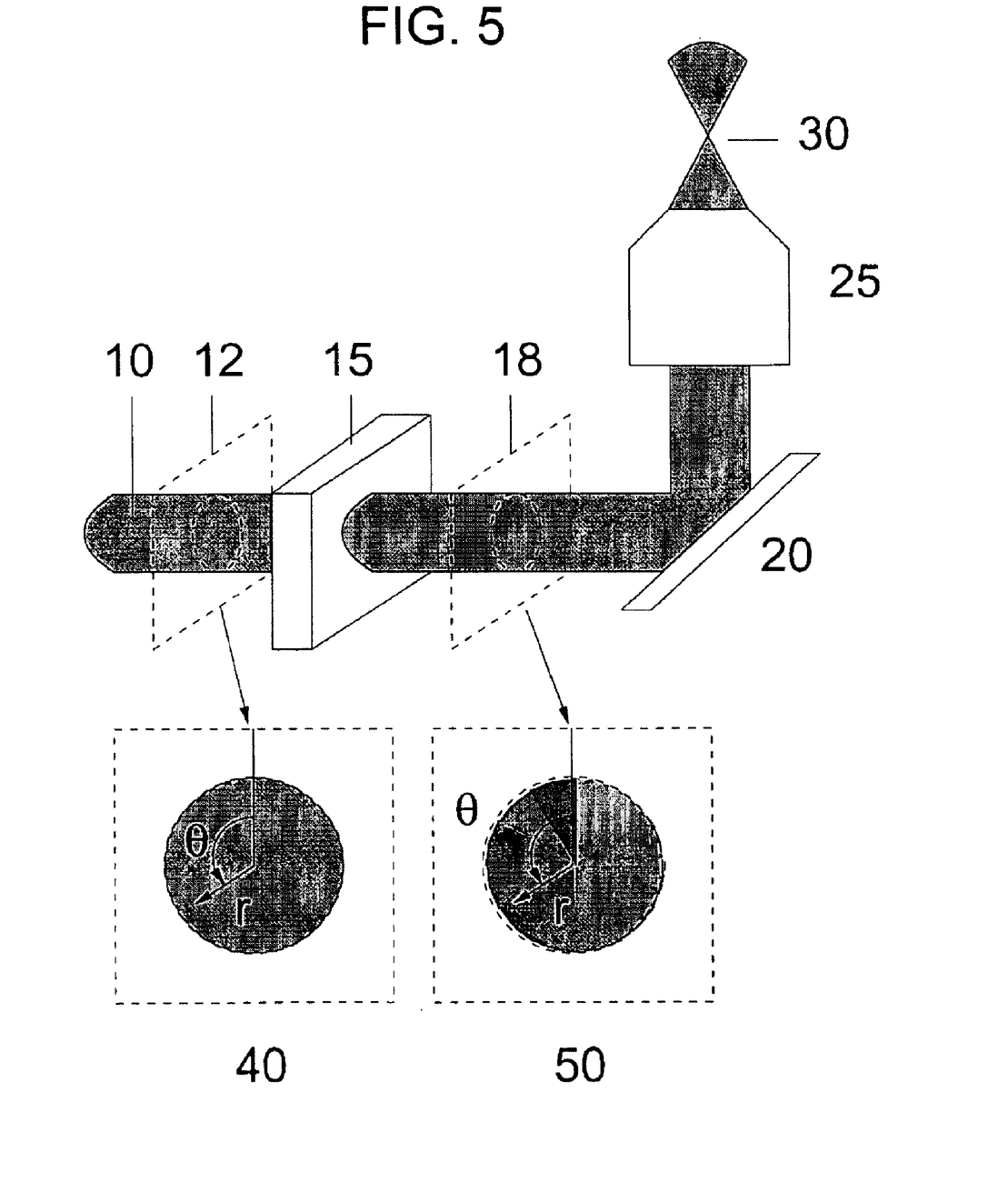
FIG. 5 is a schematic diagram of an optical train used for creating a single optical vortex trap from a collimated Gaussian laser beam.

FIG. 5 shows a conventionally-known method for converting a Gaussian beam of light into a Laguerre-Gaussian beam useful for forming optical vortices. As shown in FIG. 5, the Gaussian beam 10 propagates from the left to the right. When viewed in a cross-section 12, the Gaussian beam 10 has a uniform and constant phase, as indicated schematically in an inset 40. After passing through an appropriately designed diffractive optical element 15, the Gaussian beam 10 acquires a phase which precesses around the optical axis, and thus is converted into a Laguerre-Gaussian beam. When viewed at a cross-section 18, the phase varies across the wavefront as shown in inset 50. The modified beam then is reflected by a mirror 20 into the back aperture of a strongly converging focusing element 25. This strongly converging focusing element 25 brings the beam 10 to a focus 30. The focus 30 is the location of the optical vortex.

The diffractive optical element 15 is preferably chosen from the class of phase modifying diffractive optical elements, rather than from the class of amplitude or mixed phase-amplitude diffractive optical elements. A diffractive optical element which modifies the amplitude of the beam 10 must reduce its amplitude, thereby reducing the intensity and lowering the overall efficiency of the optical train. A phase-only diffractive optical element, on the other hand, can operate on the beam 10 without reducing the intensity. In the case of a phase-only diffractive optical element, the diffractive optical element needs to convert a $TEM_{00}$ Gaussian beam into a Laguerre-Gaussian beam of topological charge l and thus must shift the beam's phase by an amount:

$$\phi_l(\vec{\rho}) = l\theta \bmod 2\pi \quad (8)$$

In this situation, the center (r=0) of the phase pattern is aligned with the axis of the beam.

A practical phase hologram, such as a practical phase hologram implemented using a phase-shifting spatial light modulator, cannot implement any arbitrary amount of phase shift. Rather, such practical phase holograms are typically designed to implement discrete values of a phase shift between 0 and a maximum phase shift of $2\pi$ radians. In such an example, the required phase shift is modified to account for the following particular consideration:

$$\phi_q(\vec{r}) = q\theta \bmod 2\pi \quad (9)$$

A diffractive optical element of the type described above creates an approximation to a Laguerre-Gaussian beam coaxial with the initial Gaussian beam. Such an arrangement is undesirable in some circumstances, and deflecting the Laguerre-Gaussian beam away from the initial input beam can be preferable. In such a case, the desired phase profile can be modified to:

$$\phi_q(\vec{r}) = (\vec{k} \cdot \vec{r} + l\theta) \bmod 2\pi \quad (10)$$

In the above situation, the angular deflection of the Laguerre-Gaussian beam is given by $\sin^{-1}(k\lambda)$, with $k = |\vec{k}|$, for light of wavelength $\lambda$. This phase function is capable of creating a single displaced optical vortex from a single input Gaussian beam.

Figure 6:
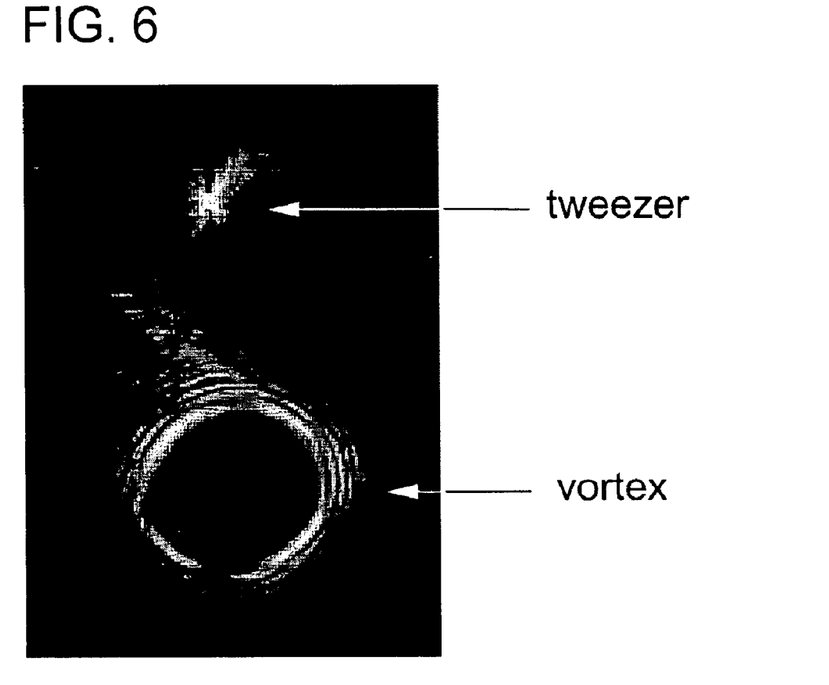
FIG. 6 is a photomicrograph of a conventional optical tweezer focused into the same plane as an optical vortex with l=60.

FIG. 6 is a photomicrograph of a conventional optical tweezer focused into the same plane as an optical vortex with l=60. The apparently nonuniform intensity along the rim of the vortex is a polarization-dependent artifact of the imaging system and not an inherent property of the vortex or of its implementation.

The mirror 20 as shown in FIG. 5 may be chosen such that light collected by the focusing element passes through the mirror 20 to an imaging system. For example, a dichroic mirror 20 can be chosen to reflect the wavelength of laser light while allowing other wavelengths to pass therethrough for imaging. If the mirror 20 is only partially reflective, some of the laser light scattered by a sample at a point 30 can pass back through the mirror to create an image of the optical vortex itself. FIG. 6 shows such a picture with the point-like focus of a conventional optical tweezer contrasted with the diffraction-limited ring-focus of an optical vortex of l=60.

Notably, the largest topological charge reported previously has l=3 and was implemented with a photolithographically fabricated diffractive optical element. Optical vortices implemented in accordance with the present invention, however, have included topological charges exceeding l=160 using a dynamic spatial light modulator. Some useful and interesting physical effects which form the basis of the present invention only are manifested for high-charge optical vortices and so would not have been observed using conventional techniques.

It has been previously suggested that an alternative technique for reconfiguring beams of light with a spatial light modulator also is capable of creating optical vortices. The alternative is deficient, however, because the optical train does not create the phase profile of an optical vortex and therefore cannot implement the optical vortices' characteristic and useful properties. Instead, the alternative approach simply shapes the intensity of the trapping beam into an annulus. Such a shaped beam would come to a bright focus and share the properties of conventional optical tweezers.

Previous, conventional implementations have produced only single optical vortices in fixed positions. By contrast, the implementation according to the present invention builds upon the holographic optical tweezer technique and permits the creation of arbitrary three-dimensional arrangements of multiple optical vortices, each with its own specified topological charge. When implemented with a computer-addressable spatial light modulator, the same technique permits dynamical reconfiguration of the ensemble of vortices.

Optical vortices have at least two notable properties. Because all phases are present along the circumference of a Laguerre-Gaussian beam, destructive interference cancels the beam's intensity along its axis, all the way to the focus. Optical vortices thus have dark centers roughly $\lambda\sqrt{2l}$ across and are useful for trapping reflecting, absorbing or low-dielectric particles or low-dielectric particles not compatible with conventional optical tweezers. Each photon in a Laguerre-Gaussian beam also carries angular momentum $\hbar$, independent of its polarization. A particle absorbing such photons while trapped in an optical vortex therefore experiences a torque proportional to the rate at which the particle absorbs photons and the beam's topological charge l. Optical vortices are useful, therefore, for driving motion at small length scales, for example in microelectromechanical systems.

Figure 4A:
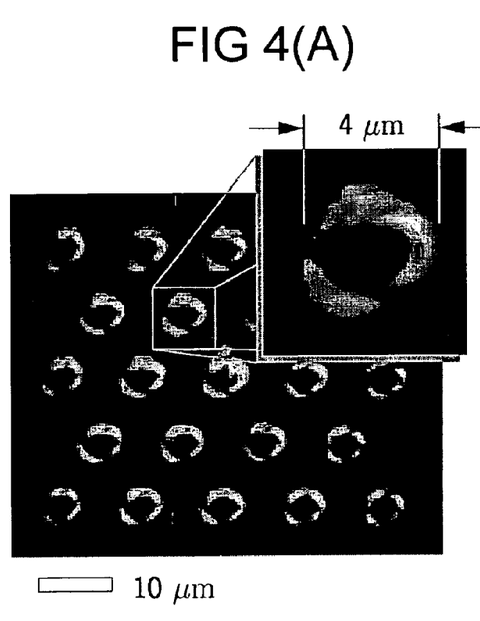
FIG. 4(A) is an image of a triangular array of optical vortices with a topological charge l=20 created from an equivalent array of tweezers.
Figure 4B:
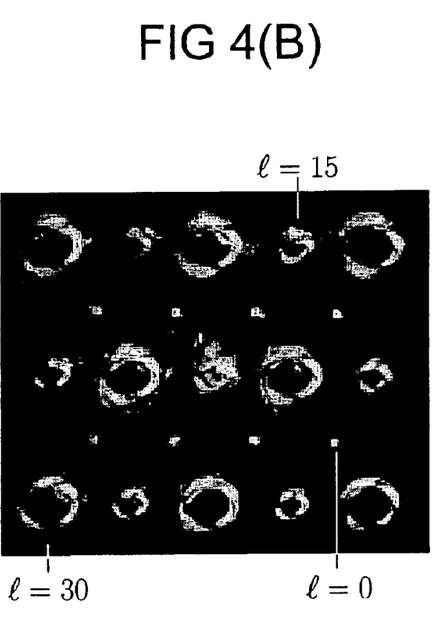
FIG. 4(B) is an image of colloidal polystyrene spheres 800 nm in diameter trapped in 3×3 square array of l=15 optical vortices.

Applying $\phi_l(\vec{\rho})$. to a kinoform encoding an array of optical tweezers yields an array of identical optical vortices, as shown in FIG. 4(A). In this case, the light from the trap array is imaged directly by reflection off a mirrored surface in the microscope's focal plane. Light from the focused optical vortices is imaged from a mirrored surface in the sample plane. The inset shows a more detailed view of one vortex's structure. FIG. 4(B) shows multiple colloidal particles trapped on the bright circumferences of a 3×3 array of l=15 vortices. Multiple particles trapped in arrays of optical vortices have remarkable cooperative behavior, particularly for large values of the topological charge l.

Figure 4C:
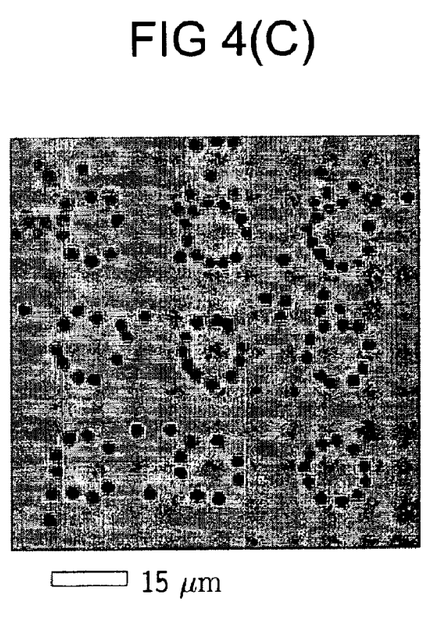
FIG. 4(C) is an image of a mixed array of optical tweezers (l=0) and optical vortices with l=15 and l=30 in the same configuration as (a), calculated with Eq. (11)

The vortex-forming phase function also can be applied to individual traps through:

$$K_j^V(\vec{r}_j, \vec{\rho}) = \exp(il_j\theta), \quad (11)$$

as demonstrated in the mixed array of optical tweezers and optical vortices shown in FIG. 4(C). $K^V$ can be combined with $K^L$ to produce three-dimensional arrays of vortices. Such heterogeneous trapping patterns are useful for organizing disparate materials into hierarchical three-dimensional structures and for exerting controlled forces and torques on extended dynamical systems.

Appropriately phased linear combinations of optical vortices and conventional tweezers have been shown to operate as optical bottles and controlled rotators. Such composite traps also can be synthesized with straightforward modifications of the algorithms discussed here. Still other phase profiles can impart new functionality. For example, the axicon profile $\phi_a(\vec{\rho}) = \gamma\rho$ converts a Gaussian beam into an approximation of a Bessel beam. Such beams come to a diffractionless focus over a range which can extend to several microns. The resulting axial line traps are useful for guiding particles in three dimensions, for aligning rod-like and elliptical samples, and for creating uniform stacks of particles. Other generalizations follow naturally with virtually any mode of light having potential applications.

Prior discussions and implementations of optical vortices emphasized the potential utility for driving microscopic machines through the transfer of torque from single optical vortices. In these cases, the use of single optical vortices of low topological charge was emphasized. The following applications take advantage of one or more properties of optical vortices and optical vortex arrays created with the holographic optical tweezer (HOT) technique.

Prior applications have used torque exerted by circularly polarized light to rotate individual components of micromachines. Using optical vortices to drive circular motion offers several advantages. By increasing the amount of angular momentum transferred per photon of absorbed light, the topological charge l reduces the power required to achieve a desired amount of torque. This phenomenon is beneficial for minimizing undesirable heating due to absorbed light as well as for reducing the power requirements and cost of the laser. Transferring the angular momentum to the rim of a micromachined gear also improves efficiency because the centers of such devices often serve as axles, bearings, or other stationary components. Light absorbed at such points contributes only to heating and is otherwise wasted.

Because of the difficulty of driving even one micromachined gear with other available techniques using conventional techniques, conventional microelectromechanical devices (MEMs) are designed to be driven at just one point. The availability of multiple independent vortices in a holographic optical tweezer system facilitates distributed driving in MEMs systems. Supplying torque to multiple stages in a complex mechanical system improves efficiency, reduces wear and reduces the requirements on the maximum torque any one component must withstand.

Optical vortices transfer torque to illuminated particles. Additionally, optical vortices also act as optical traps. Dielectric particles attracted to a bright rim of an optical vortex can be trapped in three dimensions, similar to the trapping action in an ordinary optical tweezer. Particles trapped in a vortex, however, spin on their axis at a rate governed by a balance between optical absorption and viscous drag. The spinning particles entrain flows in the surrounding fluid, and these flows can be used for several purposes.

Figure 8A:
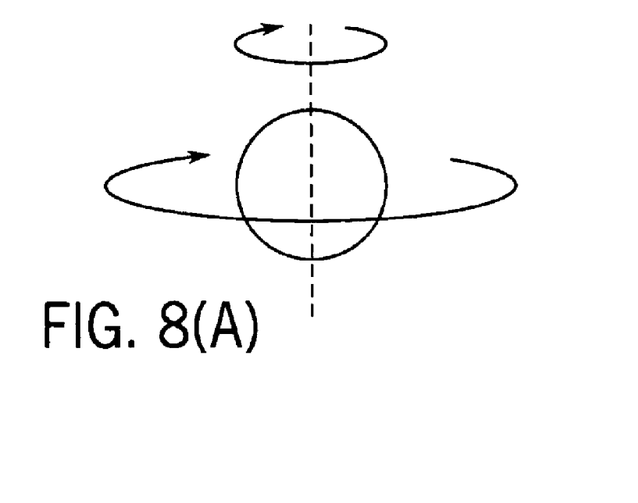
FIG. 8(A) is a schematic illustration of a single particle trapped in an optical vortex spinning about its axis and is entrained in a circulating flow of fluid.
Figure 8B:
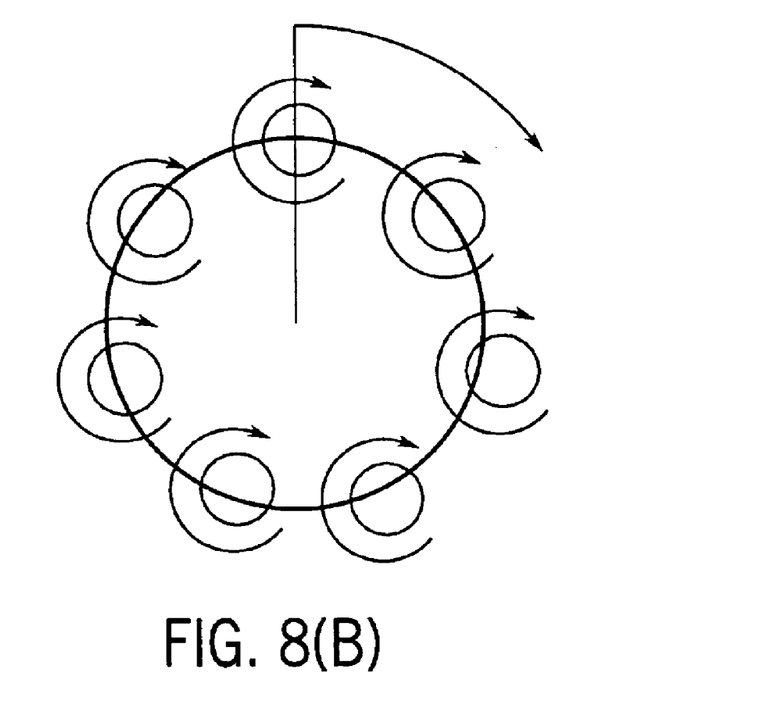
FIG. 8(B) is a schematic illustration of multiple particles trapped on the rim of an optical vortex and which interact hydrodynamically to collectively rotate about the vortex's center.
Figure 8C:
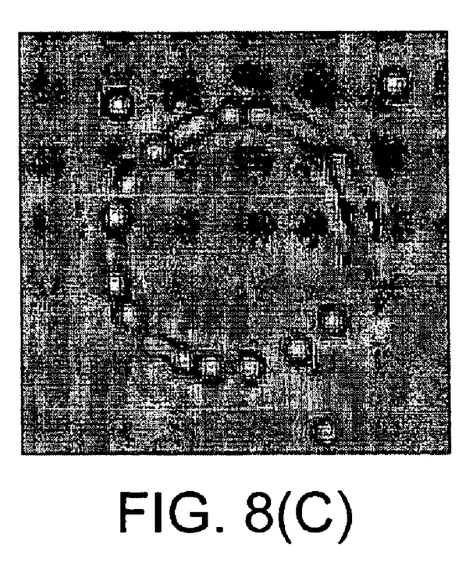
FIG. 8(C) is an illustration of a ring of colloidal silica spheres 1 $\mu$m in diameter dispersed in water and trapped in an optical vortex with l=40.

If the circumference of an optical vortex's rim is larger than the diameter of a particle, then several dielectric particles can be trapped simultaneously on the rim, each spinning on its axis. One particle spinning on the rim of an optical vortex will not spontaneously translate through the surrounding fluid. Hydrodynamic coupling among neighboring trapped particles, however, leads the entire assembly of particles to rotate around the center of the vortex. The rates of spinning and rotation can be controlled over a wide range by changing the laser's intensity while leaving all other control parameters fixed. FIG. 8(C) shows such a ring of particles created with a l=60 optical vortex. The images of the individual spheres in FIG. 8(C) are blurred because the ring rotates at roughly 100 Hz.

Figure 7:
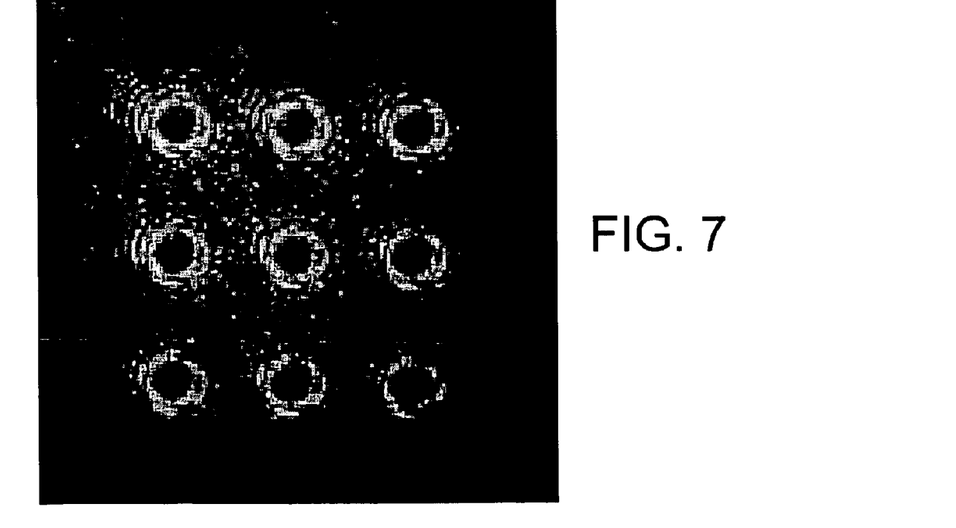
FIG. 7 is an illustration of an array of optical vortices with l=15 created by modifying a 3×3 array of conventional holographic optical tweezers using the system described in Eq. (5)
Figure 8D:
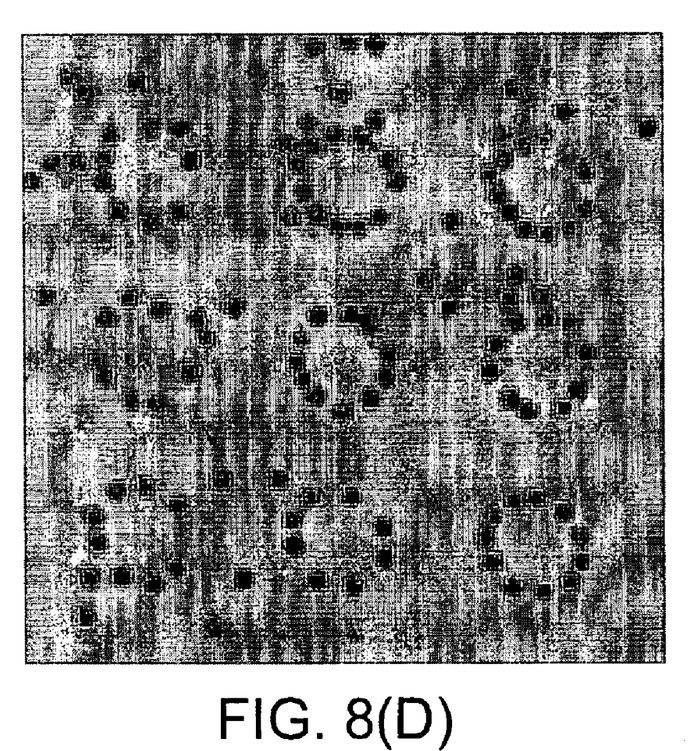
FIG. 8(D) shows a 3×3 array of optical vortices with l=15 creating and driving rings of 800 nm diameter colloidal polystyrene spheres.

The holographic optical tweezer technique can create multiple optical vortices in virtually any desired configuration. For example, FIG. 8(D) shows a 3×3 array of co-rotating rings of particles trapped in l=15 optical vortices. The array of vortices shown in FIG. 7 was used to create this micromachine. Interactions among such rings can produce cooperative effects not possible with one ring, just as trapping multiple particles in a single vortex leads to new effects not seen with a single trapped particle.

One of the principal advantages of the approach to assembling and driving micromachines described herein is that it operates with no moving parts. All of the assembly is accomplished by static optical gradient forces, and all of the motion is driven by the angular momentum inherent in the light's topological charge.

Figure 10:
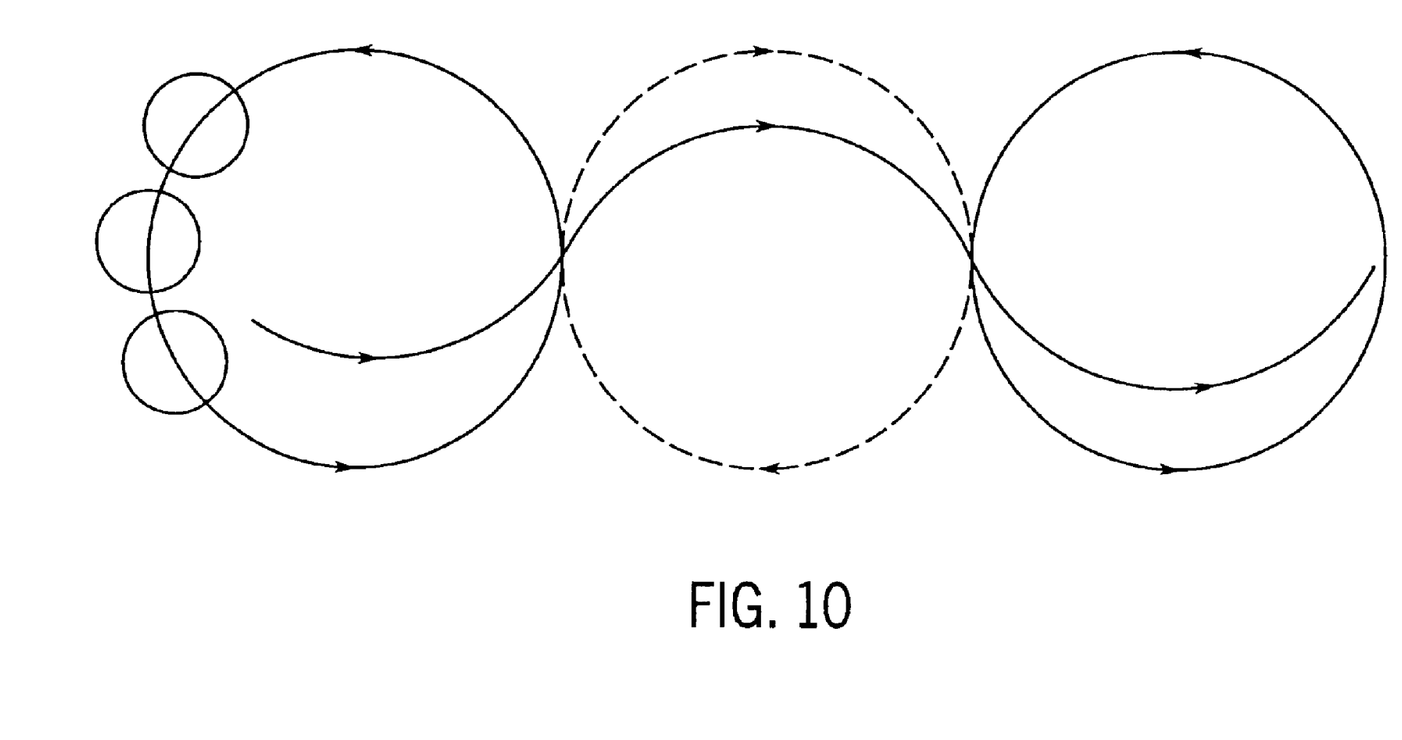
FIG. 10 is a schematic representation of optical vortices with alternating positive and negative topological charge transporting particles rapidly along a line.

The flow outside a single spinning particle or a ring of particles can be used to pump fluids through small channels. FIG. 10 schematically shows a typical implementation, with four centers of rotation entraining flow in a closed loop. Regarding the self-assembled micromachines, this application of optical vortices shown in FIG. 6 has the advantage of operating non-invasively on a closed system while relying on no moving parts. Indeed, steady-state pumping can be achieved with a single static diffractive optical element in a holographic optical tweezer optical train.

Figure 9A:
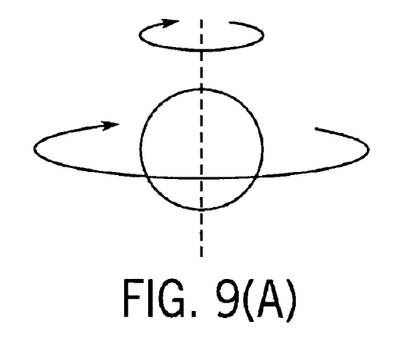
FIG. 9(A) schematically shows a spinning particle or a rotating ring of particles in an optical vortex with an entraining circulating fluid flow.
Figure 9B:
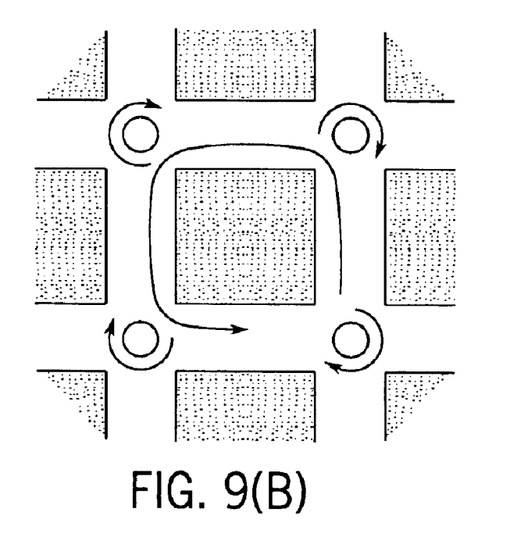
FIG. 9(B) shows a schematic superposition of flows driven by multiple spinning particles that can lead to useful fluid transport in microfluidics channels.
Figure 9C:
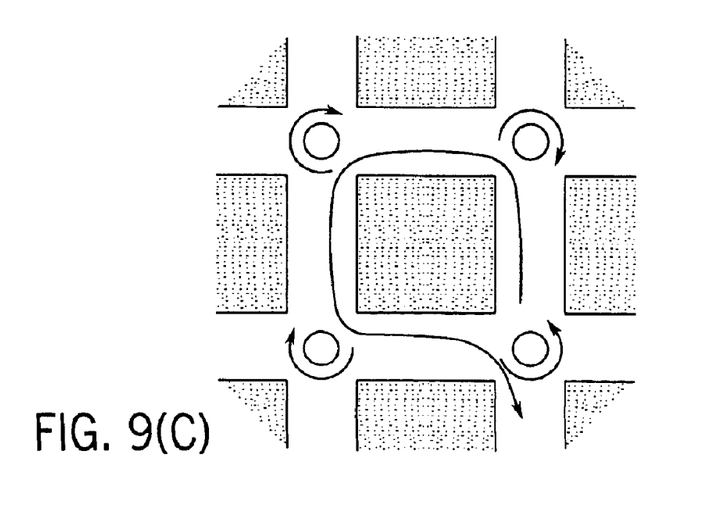
FIG. 9(C) shows schematically how reversing the sense of one particle's rotation drives the flow out one of the channels.

Having established a pumping pattern such as the example in FIG. 9(B), reversing the sense of rotation of one of the vortices results in a reconfigured pumping pattern which redirects the fluid flow. This reconfigured pattern is shown in FIG. 9(C). In FIG. 9(B), the four trapped particles (or rings) cooperate to pump fluid through a closed loop. This dynamical reconfiguration of flows can be performed in real time by changing the diffractive optical element projected in the holographic optical tweezer system.

Rotating rings of particles, such as in the examples shown in FIGS. 8(C) and 8(D), permit the entrainment of very complicated flow patterns. These flow patterns can be used to mix fluids in volumes ranging from a few hundred nanometers across to a few hundred micrometers across. Such mixing is useful in lab-on-a-chip applications for which the laminar flow in microfluidics systems generally precludes mixing.

Holographic optical tweezers are capable of placing optical vortices in virtually any desired configuration and can alternate among sequences of vortex patterns. For example, the schematic diagram shown in FIG. 10 shows three overlapping optical vortices whose topological charge alternates sign. It should be noted that, if necessary, the different types of vortices can be turned on and off alternately to produce deterministic transport favoring collections of particles of a particular size. A single particle subjected to such an intensity field will spin in place. Multiple particles, however, are driven along the rim of each vortex. Using the holographic optical tweezer technique, the vortices can be placed tangent to each other. Particles reaching the intersection will find their spin suppressed and so can be pushed by their neighbors into the vortex with alternate sense rotation. Once two or more particles have been pushed over, the collection will rotate along the rim of the second vortex, and so on. This technique allows for the rapid transport of particles along simple or complicated trajectories, with no moving parts, using a single static hologram.

Alternately turning on and off the positive and negative vortices opens up additional possibilities for dynamically selecting particles on the basis of their transit times around the vortices' rims. Such a procedure may be used as the basis of a particle fractionation technique.

It should be understood that the above description of the invention and specific examples and embodiments, while indicating the preferred embodiments of the present invention are given by demonstration and not limitation. Many changes and modifications within the scope of the present invention may be made without departing from the spirit thereof and the present invention includes all such changes and modifications.

What is claimed is:

1. A micromachine comprising:
   a diffractive optical element;
   a focused beam of laser light which interacts with the diffractive optical element to form a plurality of optical traps;
   a computer for executing a program to generate an optical vortex from the plurality of optical traps, the optical vortex thereby being used as a micromachine to manipulate a material.

2. The micromachine as defined in claim 1 wherein the diffractive optical element comprises a computer generated element.

3. The micromachine as defined in claim 1 wherein a plurality of optical vortices are included as a component of the micromachine.

4. The micromachine as defined in claim 3 wherein the plurality of optical vortices comprise a plurality of concentric rings formed from the optical traps.

5. The micromachine as defined in claim 1 wherein direction of rotation of the optical vortex can be changed by the computer executing the program.

6. The micromachine as defined in claim 1 wherein a fluid is manipulated by the optical vortex to cause fluid flow.

7. The micromachine as defined in claim 6 wherein a plurality of the optical vortex form a flow pattern enabling mixing of the fluid.

8. The micromachine as defined in claim 1 further including particles which are controllably positioned by the optical vortex to enable selected manipulation of a material disposed near the optical vortex.

9. The micromachine as defined in claim 8 wherein the particles are placed such that a plurality of optical vortices are disposed tangent to one another.

10. The micromachine as defined in claim 9 wherein the optical vortices have different rotational directions.

11. The micromachine as defined in claim 1 wherein the optical vortex acts as a trap for dielectric particles on a bright rim of the optical vortex.

12. The micromachine as defined in claim 11 wherein a plurality of the dielectric particles adjacent one another form a micromachine having cooperative hydrodynamic coupling for computer controlled vortex motion.

13. The micromachine as defined in claim 1 wherein the micromachine is disposed on a lab-on-chip to enable mixing thereon.

* * * * *